(12) United States Patent
Bernardon et al.

(10) Patent No.: US 6,992,095 B2
(45) Date of Patent: Jan. 31, 2006

(54) STILBENE COMPOUNDS COMPRISING AN ADAMANTYL GROUP, COMPOSITIONS AND METHODS THEREOF

(75) Inventors: Jean-Michel Bernardon, Le Rouet (FR); Bruno Charpentier, Biot (FR)

(73) Assignee: Galderma Research & Development, S.N.C., Valbonne Sophia Antipolis (FR)

( * ) Notice: Subject to any disclaimer, the term of this patent is extended or adjusted under 35 U.S.C. 154(b) by 29 days.

(21) Appl. No.: 10/676,089

(22) Filed: Oct. 2, 2003

(65) Prior Publication Data

US 2004/0067971 A1    Apr. 8, 2004

Related U.S. Application Data

(60) Continuation of application No. 09/788,469, filed on Feb. 21, 2001, now abandoned, which is a division of application No. 09/002,040, filed on Dec. 31, 1997, now Pat. No. 6,214,878.

(30) Foreign Application Priority Data

Dec. 31, 1996    (FR) .................................. 96 16311

(51) Int. Cl.
| | | |
|---|---|---|
| A61K 31/44 | (2006.01) | |
| A61K 31/192 | (2006.01) | |
| C07C 69/76 | (2006.01) | |
| A61P 17/00 | (2006.01) | |
| C07D 333/18 | (2006.01) | |

(52) U.S. Cl. ................. 514/354; 514/569; 514/350; 514/351; 514/356; 514/532; 514/237.5; 514/277; 424/60; 546/316; 546/318; 546/323; 546/326; 560/102; 562/492

(58) Field of Classification Search .......... 514/569, 514/350, 351, 532, 237.5, 354, 356
See application file for complete search history.

(56) References Cited

U.S. PATENT DOCUMENTS 5,124,473 A    6/1992   Shroot et al.
5,436,369 A    7/1995   Bronson et al.
5,547,983 A    8/1996   Charpentier
5,877,342 A    3/1999   Bernardon et al.

FOREIGN PATENT DOCUMENTS

| EP | 0 776 881 | 6/1997 |
| EP | 0 776 885 | 6/1997 |
| WO | 97/13505 | 4/1997 |
| WO | 98/01132 | 1/1998 |

OTHER PUBLICATIONS

Orfanos et al. Drugs. 1997, 53(3): 358-370.*
Apfel et al. Proc. Natl. Acad. Sci. USA, 1992, 89: 7129-7133.*
Charpentier et al., *J. Med. Chem.*, vol. 38, No. 26, Dec. 22, 1995, pp. 4993-5006, published by the American Chemical Society, Washington, D.C.
Sun et al., *Cancer Res.*, 57(21), 4931-4939 (1997), published by American Association for Cancer Research, Baltimore, MD.

* cited by examiner

*Primary Examiner*—Evelyn Mei Huang
(74) *Attorney, Agent, or Firm*—Buchanan Ingersoll, P.C.

(57) ABSTRACT

The invention relates to novel stilbene compounds having the general formula (I):

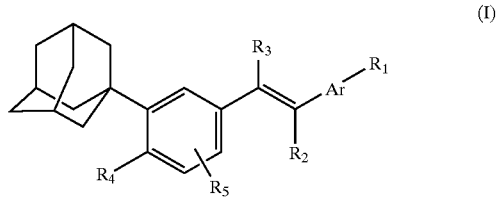

as well as to pharmaceutical compositions for use in human or veterinary medicine, including dermatological, rheumatic, respiratory, cardiovascular and ophthalmic conditions and cosmetic compositions and methods of use thereof.

4 Claims, 2 Drawing Sheets

STILBENE COMPOUNDS COMPRISING AN ADAMANTYL GROUP, COMPOSITIONS AND METHODS THEREOF

CROSS-REFERENCE TO RELATED APPLICATIONS

This application is a continuation of U.S. patent application Ser. No. 09/788,469, filed Feb. 21, 2001, now abandoned, which is a divisional of U.S. patent application Ser. No. 09/002,040, filed Dec. 31,1997, now U.S. Pat. Ser. No. 6,214,878 B1.

BACKGROUND OF THE INVENTION

Technical Field of the Invention

The invention relates to stilbene compounds containing an adamantyl group which are novel and useful industrial products. The invention also relates to the use of these novel compounds in pharmaceutical compositions intended for use in human or veterinary medicine, or alternatively, in cosmetic compositions.

SUMMARY OF THE INVENTION

The compounds according to the present invention have pronounced activity in the fields of cell proliferation and differentiation, and find application more particularly in the topical and systemic treatment of dermatological complaints associated with a keratinization disorder, dermatological (or other) complaints with an inflammatory and/or immunoallergic component, and dermal or epidermal proliferations, whether benign or malignant. These compounds can also be used in the treatment of degenerative diseases of connective tissue, to combat aging of the skin, both light-induced and chronological aging, and to treat cicatrization disorders. They also find application in the ophthalmic field, in particular, in the treatment of corneopathies.

The compounds according to the present invention can also be used in cosmetic compositions for body and hair hygiene.

The compounds according to the invention can be represented by the general formula (I) below:

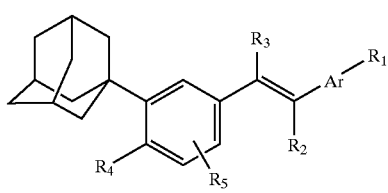

(I)

wherein:

$R_1$ represents
  (i) the —$CH_3$ radical,
  (ii) the radical —$CH_2$—O—$R_6$,
  (iii) the radical —O—$R_6$, or
  (iv) the radical —CO—$R_7$,
  wherein the radicals $R_6$ and $R_7$ have the meanings given below, Ar represents a radical of formulae (a) to (f) below:

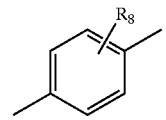
(a)

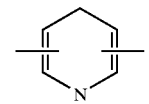
(b)

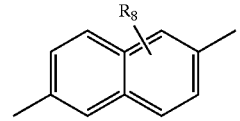
(c)

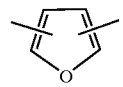
(d)

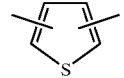
(e)

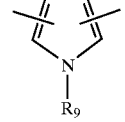
(f)

wherein $R_8$ and $R_9$ have the meanings given below, $R_2$ and $R_3$, which may be identical or different, independently represent a hydrogen atom or a lower alkyl radical, $R_4$ represents the radical —$(X)_m$—$(CH_2)_n$—Y—$(CH_2)_p$—$R_{10}$,
  wherein the values m, n and p and the radicals X, Y and $R_{10}$ having the meanings-given below, $R_5$ represents a hydrogen or halogen atom, a lower alkyl radical or a radical —O—$R_6$, $R_6$ represents a hydrogen atom, a lower alkyl radical or a radical —CO—$R_{11}$, $R_7$ represents a hydrogen atom, a lower alkyl radical, a radical —$OR_{12}$ or a radical

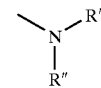

wherein R' and R", which may be identical or different, independently represent a hydrogen atom, a lower alkyl radical, a mono- or polyhydroxyalkyl radical, an optionally substituted aryl radical or an amino acid or peptide or sugar residue, or alternatively, taken together, form a heterocycle, it being understood that, in all of the text hereinabove:
  m is an integer ranging from 0 to 1,
  n is an integer ranging from 1 to 6, inclusive,
  p is an integer ranging from 1 to 6, inclusive,
  X represents O or $S(O)_q$,
  Y represents O, $S(O)_q$ or N—$R_9$,
  q is an integer ranging from 0 to 2, inclusive, $R_8$ represents a hydrogen or halogen atom, a lower alkyl radical or a radical —O—$R_6$, $R_9$ represents a hydrogen atom, a lower alkyl radical or a radical —CO—$R_{11}$, $R_{10}$ represents a mono- or polyhydroxyalkyl radical wherein the hydroxyls are optionally protected in the form of methoxy, ethoxy, acetoxy or acetonide, a radical —CO—$R_7$ or an optionally substituted aryl or aralkyl radical, $R_{11}$ represents a lower alkyl radical, $R_{12}$ represents a hydrogen atom, an alkyl radical, an alkenyl radical, a mono- or polyhydroxyalkyl radical in which the hydroxyls are optionally protected in the form of methoxy, ethoxy, acetoxy or acetonide, an optionally substituted aryl or aralkyl radical, a sugar residue or an amino acid or peptide residue, and the optical and geometrical isomers of the compounds of formula (I), as well as the salts thereof.

Figure 1:
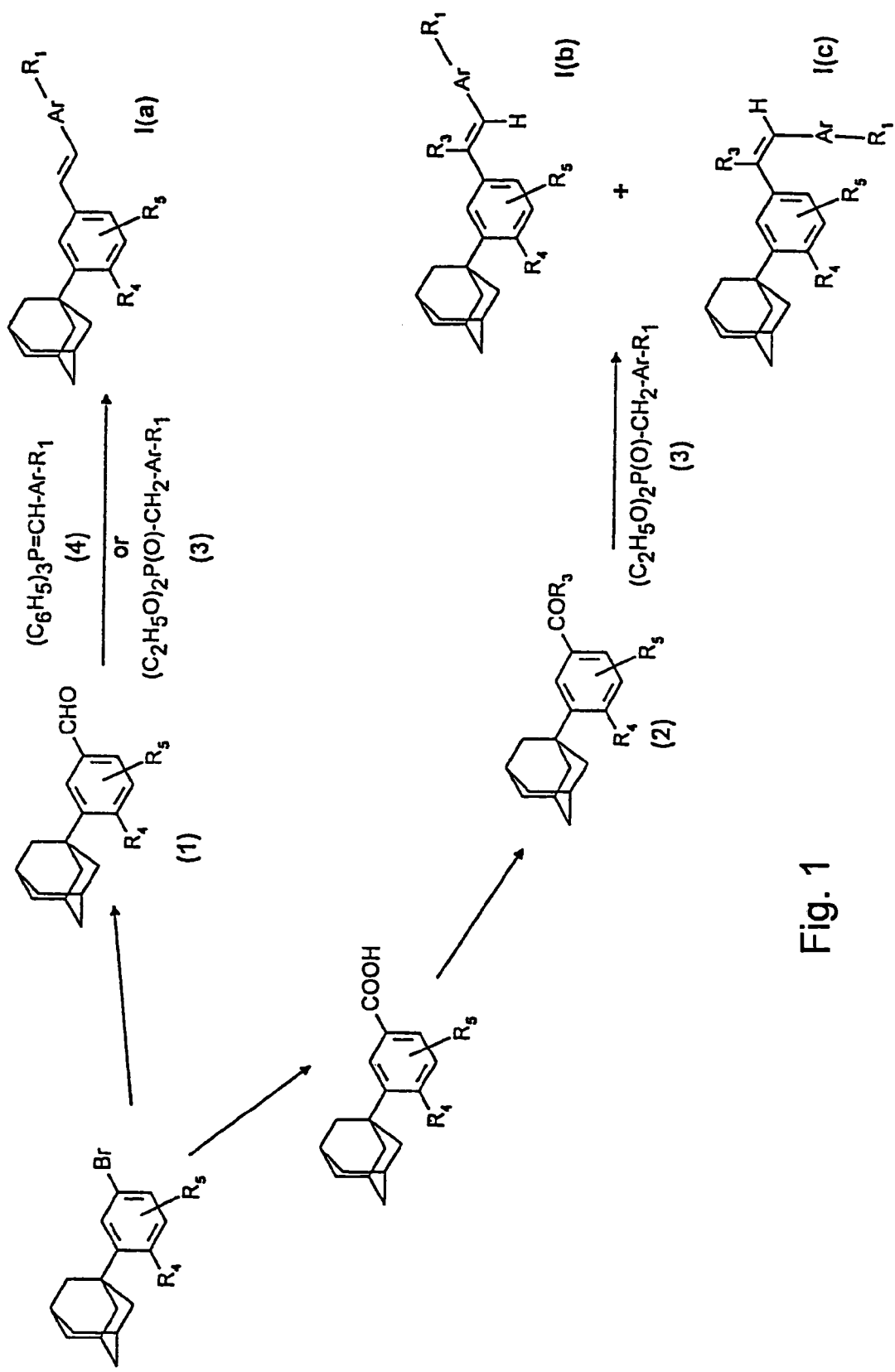
FIG. 1 is a schematic diagram of a process for preparing the compounds of formulae I(a), I(b) and I(c).

DETAILED DESCRIPTION OF BEST MODE AND SPECIFIC/PREFERRED EMBODIMENTS OF THE INVENTION

When the compounds according to the is invention are in the form of salts resulting from the addition of an acid, the salts are pharmaceutically or cosmetically acceptable salts obtained by addition of an inorganic or organic acid, in particular, hydrochloric acid, sulfuric acid, acetic acid, citric acid, fumaric acid, hemisuccinic acid, maleic acid or mandelic acid. When the compounds according to the invention are in the form of salts resulting from the addition of a base, those salts are preferably salts of an alkali metal or alkaline earth metal, or alternatively, salts of zinc or of an organic amine.

According to the present invention, the term alkyl radical is understood to refer to a linear or branched radical optionally substituted with one or more halogen atoms having from 1 to 20, preferably from 1 to 12, carbon atoms, advantageously the methyl, ethyl, isopropyl, butyl, tert-butyl, hexyl, nonyl and dodecyl radicals. When it is lower, the alkyl radical generally comprises from 1 to 10 carbon atoms, preferably from 1 to 6 carbon atoms. Exemplary lower alkyl comprise methyl, ethyl, propyl, isopropyl, tert-butyl and hexyl radicals.

Exemplary linear alkyl radicals having from 1 to 20 carbon atoms comprise methyl, ethyl, propyl, 2-ethylhexyl, octyl, dodecyl, hexadecyl and octadecyl radicals.

Exemplary branched alkyl radicals having from 1 to 20 carbon atoms comprise 2-methylpentyl, 1-methylhexyl and 3-methylheptyl radicals.

By the term "alkenyl radical" is intended a linear or branched radical having from 2 to 20 carbon atoms containing one or more double bonds.

The preferred alkenyl radical is a radical ranging from 2 to 5 carbon atoms and having one or more ethylenic unsaturations, more preferably the allyl radical.

By the term "monohydroxyalkyl or polyhydroxyalkyl radical" is intended a radical containing from 1 to 6 carbon atoms and from 1 to 5 hydroxyl groups.

The preferred monohydroxyalkyl radical comprises a radical ranging from 1 to 3 carbon atoms, in particular the hydroxymethyl, 2-hydroxyethyl and 2- or 3-hydroxypropyl radicals.

The preferred polyhydroxyalkyl radical comprises a radical having from 3 to 6 carbon atoms and from 2 to 5 hydroxyl groups, for example, the 2,3-dihydroxypropyl, 2,3,4-trihydroxybutyl or 2,3,4,5-tetrahydroxypentyl radicals or the pentaerythritol residue.

The preferred aryl radical comprises a phenyl radical optionally substituted with at least one halogen atom, a hydroxyl radical, an alkyl radical, a nitro function, a methoxy group or an optionally substituted amine function.

The preferred aralkyl radical comprises the benzyl or phenethyl radical optionally substituted with at least one halogen atom, a hydroxyl radical, a nitro function or a methoxy group.

By the term "sugar residue" is intended a residue derived in particular from glucose, galactose or mannose, or alternatively from glucuronic acid.

By the term "amino acid residue" is intended a residue derived from one of the amino acids, for example, lysine, glycine or aspartic acid, and by the term "peptide residue" is intended a dipeptide or tripeptide residue resulting from the combination of amino acids.

By the term "heterocycle" is intended a piperidino, morpholino, pyrrolidino or piperazino radical, optionally substituted in position 4 with a $C_1$–$C_6$ alkyl or polyhydroxyalkyl radical as defined above.

When the radicals $R_5$ and $R_8$ represent a halogen atom, the halogen atom is preferably a fluorine, bromine or chlorine atom.

Particular compounds of formula (I) according to the present invention comprise:

Ethyl 4-[(E)-2-(3-(1-adamantyl)-4-methoxyethoxy-methoxyphenyl)ethenyl]benzoate.

4-[(E)-2-(3-(1-Adamantyl)-4-methoxyethoxymethoxy-phenyl)ethenyl]benzoic acid.

Ethyl 4-[(E)-2-(3-(1-adamantyl)-4-methoxyethoxy-methoxyphenyl)-1-propenyl]benzoate.

4-[(E)-2-(3-(1-Adamantyl)-4-methoxyethoxymethoxy-phenyl)-1-propenyl]benzoic acid.

4-[(Z)-2-(3-(1-Adamantyl)-4-methoxyethoxymethoxy-phenyl)-1-propenyl]benzoic acid.

Methyl 5-{2-[3-adamant-1-yl-4-(2-methoxyethoxy-methoxy)phenyl]propen-(E)-yl}pyridine-2-carboxylate.

5-{2-[3-Adamant-1-yl-4-(2-methoxyethoxymethoxy)-phenyl]propen-(E)-yl}pyridine-2-carboxylic acid.

5-{2-[3-Adamant-1-yl-4-(2-methoxyethoxymethoxy)-phenyl]propen-(Z)-yl}pyridine-2-carboxylic acid.

Ethyl 6-{2-[3-adamant-1-yl-4-(2-methoxyethoxymethoxy)-phenyl]propen-(E)-yl}nicotinate.

6-{2-[3-Adamant-1-yl-4-(2-methoxyethoxymethoxy)-phenyl]propen-(E)yl}nicotinic acid.

6-{2-[3-Adamant-1-yl-4-(2-methoxyethoxymethoxy)-phenyl]propen-(Z)-yl}nicotinic acid.

Methyl 4-{2-[3-adamant-1-yl-4-(2-methoxyethoxy-methoxy)phenyl]propen-(Z)-yl}-2-methoxybenzoate.

4-{2-[3-Adamant-1-yl-4-(2-methoxyethoxymethoxy)-phenyl]propen-(E)-yl}-2-methoxybenzoic acid.

4-{2-[3-Adamant-1-yl-4-(2-methoxyethoxymethoxy)-phenyl]propen-(Z)-yl}-2-methoxybenzoic acid.

Ethyl 4-{2-[3-adamant-1-yl-4-(3-ethoxymethoxypropyl)-phenyl]propen-(E/Z)-yl}benzoate.

4-{2-[3-Adamant-1-yl-4-(3-ethoxymethoxypropyl)phenyl]-propen-(E)-yl}benzoic acid.

4-{2-[3-Adamant-1-yl-4-(3-ethoxymethoxypropyl)phenyl]-propen-(Z)-yl}benzoic acid.
Ethyl 4-{2-[3-adamant-1-yl-4-(3-benzyloxypropyl)-phenyl]propen-(E/Z)-yl}benzoate.
4-{2-[3-Adamant-1-yl-4-(3-benzyloxypropyl)phenyl]-propen-(E)-yl}benzoic acid.
4-{2-[3-Adamant-1-yl-4-(3-benzyloxypropyl)phenyl]-propen-(Z)-yl}benzoic acid.
Ethyl 4-{2-[3-adamant-1-yl-4-(3-diethylcarbamoyl-methoxypropyl)phenyl]propenyl}benzoate.
4-{2-[3-Adamant-1-yl-4-(3-diethylcarbamoylmethoxy-propyl)phenyl]propenyl)}benzoic acid.
Ethyl 4-{2-[3-adamant-1-yl-4-(3-carboxymethoxypropyl)-phenyl]propenyl}benzoate.
4-{2-[3-Adamant-1-yl-4-(3-carboxymethoxypropyl)-phenyl]propenyl}benzoic acid.
Ethyl 4-{2-[3-adamant-1-yl-4-(3-carbamoylmethoxy-propyl)phenyl]propenyl}benzoate.
4-{2-[3-Adamant-1-yl-4-(3-carbamoylmethoxypropyl)-phenyl]propenyl}benzoic acid.
N-Ethyl-4-[(E)-2-(3-(1-adamantyl)-4-methoxyethoxymethoxyphenyl)-1-propenyl]benzamide.
4-[(E)-2-(3-(1-Adamantyl)-4-methoxyethoxymethoxy-phenyl)-1-propenyl]benzamide.
N-4-(Hydroxyphenyl)-4-[(E)-2-(3-(1-adamantyl)-4-methoxyethoxymethoxyphenyl)-1-propenyl]benzamide.
4-[(E)-2-(3-(1-Adamantyl)-4-methoxyethoxymethoxy-phenyl)-1-propenyl]benzenemethanol.
4-[(E)-2-(3-(1-Adamantyl)-4-methoxyethoxymethoxy-phenyl)-1-propenyl]benzaldehyde.
4-[(E)-2-(3-(1-Adamantyl)-4-methoxyethoxymethoxy-phenyl)-1-propenyl]phenol. 4-[(E)-2-(3-(1-Adamantyl)-4-methoxyethoxymethoxy-phenyl)-1-propenyl]benzoic acid morpholide.
4-[(E)-2-(3-(1-Adamantyl)-4-methoxyethoxymethyl-sulphanylphenyl)-1-propenyl]benzoic acid.

According to the present invention, the preferred compounds of formula (I) are those for which at least one, and more preferably all, of the conditions below apply:
$R_1$ is the radical —CO—$R_7$,
Ar represents the radicals of formula (a) or (b),
X and Y, which may be identical or different, independently represent oxygen or sulfur atoms,
$R_3$ represents a lower alkyl radical.

Figure 2:
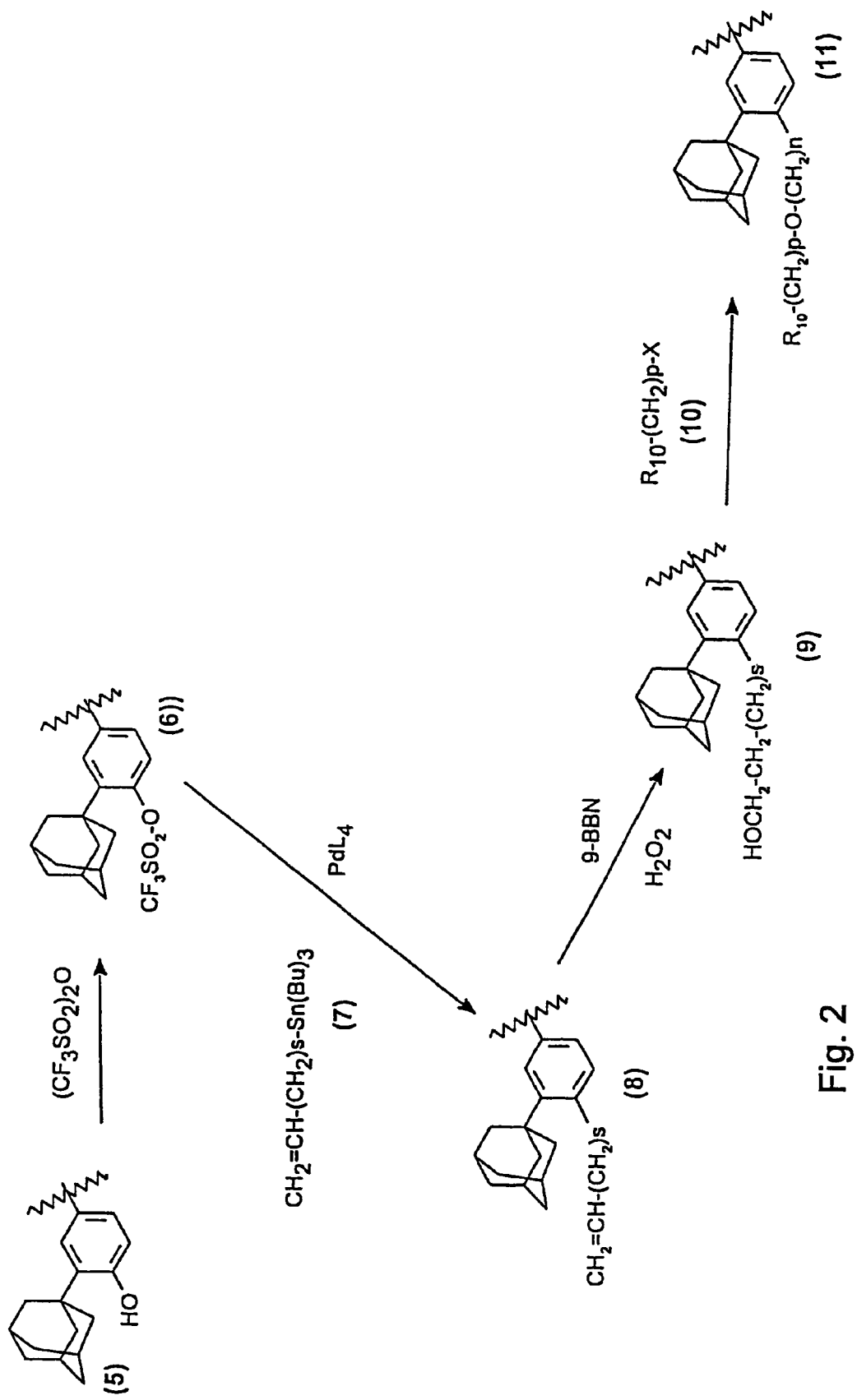
FIG. 2 is a schematic diagram of a process for preparing a halogenated compound of the present invention.

The subject of the present invention is also a process for the preparation of the compounds of formula (I), in particular, according to the reaction schemes set forth in FIGS. 1 and 2.

Thus, the compounds of formula I(a), I(b) and I(c) can be obtained (FIG. 1) by reacting, in an anhydrous medium in an organic solvent, preferably THF, an aromatic aldehyde derivative (1) (when $R_3$ is a hydrogen atom) or an aromatic ketone derivative (2) (when $R_3$ is a lower alkyl radical) in a Horner-Emmons or Wittig type reaction with aromatic phosphonate derivatives (3) or aromatic phosphine derivatives (4) in the presence of sodium hydride or potassium tert-butoxide.

In these olefination reactions, the geometrical isomer having an E configuration can also be obtained by conversion of the isomer, having a Z configuration by irradiation under UV light.

When $R_4$ represents the radicals —$(CH_2)_n$—Y—$(CH_2)_p$—$R_{10}$, the compounds can be obtained (FIG. 2) from phenol derivatives (5) which are converted into triflate derivatives (6), followed by a reaction with a tin derivative (7) in the presence of a palladium catalyst (for example bis(triphenylphosphine)palladium(II) chloride according to M. Echavaren and J. K. Stille, *J. Am. Chem. Soc.*, 109, 5478–86 (1987)). The alcohol derivatives (9) are obtained by reaction of the ethylenic derivatives (8) with 9-borabicyclo[3.3.1]nonane, followed by oxidation with aqueous hydrogen peroxide solution, according to E. F. Knights et al., *J. Am. Chem. Soc.*, 90, 5281 (1968). By alkylation with a halogenated derivative (10), the derivatives (11) are obtained. When $R_1$ represents the —COOH radical, the compounds are prepared by protecting $R_1$ with a protecting group of the alkyl, allylic or tert-butyl type. Passage to the free form can be carried out:

in the case of an alkyl protecting group, using sodium hydroxide or lithium hydroxide in an alcoholic solvent, such as methanol, or in THF,
in the case of an allylic protecting group, using a catalyst, such as certain transition metal complexes, in the presence of a secondary amine such as morpholine,
in the case of a protecting group of tert-butyl type, using trimethylsilyl iodide.

When $R_1$ is an alcohol radical, the compounds can be obtained from the acid by reduction in the presence of lithium aluminum hydride.

When $R_1$ is an aldehyde radical, the compounds can be obtained from the alcohol by oxidation with manganese oxide or pyridinium dichromate.

When $R_1$ is a radical of the amide type, the compounds can be prepared by conversion of the acid into the acid chloride, for example, with thionyl chloride, followed by reaction with aqueous ammonia or a suitable amine.

The products of general formula (I) can serve as starting materials for the manufacture of other compounds of formula (I) according to the invention. These compounds are obtained according to the standard synthetic methods used in chemistry, such as those described in "Advanced Organic Chemistry" by J. March; John Wiley and Sons (1985).

For example, functional modifications of the group $R_1$ can be carried out as indicated below:

| | | |
|---|---|---|
| carboxylic acid | → | ester |
| ester | → | carboxylic acid |
| acid | → | acid chloride |
| acid chloride | → | amide |
| acid | → | amide |
| acid | → | alcohol |
| alcohol | → | aldehyde |
| amide | → | amine |
| thiol | → | thioether |
| thioether | → | sulfoxide |
| thioether | → | sulfone |
| sulfonic acid | → | sulfonic ester |
| sulfonic acid | → | sulfonamide |
| sulfinic acid | → | sulfinic ester |

The compounds according to the invention show activity in the test of differentiation of mouse embryonic teratocarcinoma cells (F9) (*Cancer Research*, 43, 5268 (1983)) and/or in the test of inhibition of ornithine decarboxylase after induction with TPA in mice (*Cancer Research*, 38, 793–801 (1978)). These tests show the activities of these compounds in the fields of cell differentiation and cell proliferation, respectively. In the test of cell (F9) differentiation, an agonist activity may be evaluated as an antagonist activity to retinoic acid receptors. This is because an antagonist is inactive when it is alone in this test, but partially or totally inhibits the effect produced by a retinoid which is an agonist towards the morphology and secretion of the plasminogen activator. Some of these compounds are thus also active in a test which is used to identify molecules which are RAR antagonists, as described in French patent application No. 95/07302 filed on 19 Jun. 1995 by the same Assignee as the present invention, which is incorporated by reference in its entirety herein. This test comprises the following steps: (i) a sufficient amount of an RAR-agonist molecule is applied topically to a part of the skin of a mammal, (ii) a molecule capable of exhibiting RAR-antagonist activity is administered systemically or topically to this same mammal or to this same part of the skin of the mammal, before, during or after step (i), and (iii) the response on that part of the mammal's skin which has been treated is evaluated. Thus, the response to a topical application, to the ear of a mammal, of an RAR-agonist molecule, which corresponds to an increase in the thickness of this ear, may be inhibited by the systemic or topical administration of an RAR-antagonist molecule. In addition, some of these compounds may provide synergism to the biological activity of products binding to the nuclear receptors.

The subject of the present invention is also, a pharmaceutical or cosmetic composition comprising the compounds of formula (I) as defined above in combination with a pharmaceutically or cosmetically acceptable carrier therefor.

The compounds according to the present invention are particularly useful in the following fields of treatment: (1) for treating dermatological conditions associated with a keratinization disorder which has a bearing on cell differentiation and on proliferation, in particular for treating common acne, comedones, polymorphonuclear leucocytes, acne rosacea, nodulocystic acnei acne conglobata, senile acne and secondary acnes such as solar acne, medication-induced acne or occupational acne, (2) for treating other types of keratinization disorders, in particular ichthyosis, ichthyosiform states, Darrier's disease, palmoplantar keratoderma, leucoplasias and leucoplasiform states, and cutaneous or mucous (buccal) lichen, (3) for treating other dermatological complaints associated with a keratinization disorder having an inflammatory and/or immunoallergic component and, in particular, all forms of psoriasis, whether it is cutaneous, mucous or ungual psoriasis, and even psoriatic rheumatism, or alternatively cutaneous atopy, such as eczema, or respiratory atopy or alternatively gingival hypertrophy; the compounds may also be used in certain inflammatory complaints which do not exhibit a disorder of keratinization, (4) for treating all dermal or epidermal proliferations, whether benign or malignant and whether or not they are of viral origin, such as common warts, flat warts and verruciform epidermodysplasia, it being also possible for the oral or florid papillomatoses and the proliferations to be induced by ultraviolet radiation, in particular in the case of basocellular and spinocellular epitheliomas, (5) for treating other dermatological disorders such as bullosis and collagen diseases, (6) for treating certain ophthalmological disorders, in particular corneopathies, (7) for repairing or combating both light-induced and chronologic aging of the skin or for reducing actinic keratoses and pigmentations, or any pathology associated with chronological or actinic ageing, (8) for preventing or curing the stigmata of epidermal and/or dermal atrophy induced by local or systemic corticosteroids, or any other form of skin atrophy, (9) for preventing or treating cicatrization disorders or for preventing or repairing stretch marks, (10) for combating disorders of sebaceous functioning such as the hyperseborrhea of acne or simple seborrhea, (11) in the treatment or prevention of cancerous or precancerous states, (12) in the treatment of inflammatory complaints such as arthritis, (13) in the treatment of any complaint of viral origin on the skin or generally, such as Kaposi's syndrome, (14) in the prevention or treatment of alopecia, (15) in the treatment of dermatological or general complaints having an immunological component, (16) in the treatment of complaints of the cardiovascular system such as arteriosclerosis or hypertension, as well as insulin-independent diabetes, (17) in the treatment of skin disorders due to exposure to UV radiation.

In the therapeutic fields mentioned above, the compounds according to the invention may advantageously be employed in combination with other compounds having retinoid-type activity, with D vitamins or derivatives thereof, with corticosteroids, with anti-free-radical agents, α-hydroxy or α-keto acids or derivatives thereof, or alternatively with ion-channel blockers. The expression D vitamins or derivatives thereof is understood to refer, for example, to vitamin D2 or D3 derivatives and in particular 1,25-dihydroxy vitamin D3. The expression anti-free-radical agent is understood to refer, for example, to α-tocopherol, superoxide dismutase, ubiquinol or certain metal-chelating agents. The expression α-hydroxy or α-keto acids or derivatives thereof is understood to refer, for example, to lactic acid, malic acid, citric acid, glycolic acid, mandelic acid, tartaric acid, glyceric acid or ascorbic acid or salts, amides or esters thereof. Lastly, the expression ion-channel blockers is understood to refer, for example, to minoxidil (2,4-diamino-6-piperidinopyrimidine 3-oxide) and derivatives thereof.

The subject of the present invention is also a medicinal composition comprising at least one compound of formula (I) as defined above, one of the optical or geometrical isomers thereof or one of the salts thereof, in combination with a pharmaceutically or cosmetically acceptable carrier therefor.

The subject of the present invention is thus a novel medicinal composition intended in particular for treating the above-mentioned complaints, and which comprises, in a pharmaceutically acceptable support or carrier which is compatible with the mode of administration selected for this composition, at least one compound of formula (I), one of the optical or geometrical isomers thereof or one of the salts thereof.

The compounds according to the invention may be administered enterally, parenterally, topically or ocularly.

Via the enteral route, the medicinal products may be in the form of tablets, gelatin capsules, sugar-coated tablets, syrups, suspensions, solutions, powders, granules, emulsions, microspheres or nanospheres or polymeric or lipid vesicles which allow controlled release. Via the parenteral route, the compositions may be in the form of solutions or suspensions for infusion or for injection.

The compounds according to the invention are generally administered at a daily dose of about 0.01 mg/kg to 100 mg/kg of body weight, taken in 1 to 3 doses.

Via the topical route, the pharmaceutical compositions based on compounds according to the invention are more particularly intended for treating the skin and mucous membranes and may, in this case, be in the form of an ointment, cream, milk, salve, powder, impregnated pad, solution, gel, spray, lotion or suspension. They may also be in the form of microspheres or nanospheres or polymeric or lipid vesicles or polymeric patches and hydrogels which allow controlled release. These topical route compositions may moreover be either in anhydrous form or in an aqueous form, depending on the clinical indication.

Via the ocular route, they are primarily administered as eyedrops.

The compositions for topical or ocular use contain at least one compound of formula (I) as defined above, or one of the optical or geometrical isomers thereof, or alternatively one of the salts thereof, at a concentration preferably ranging from 0.001% to 5% by weight relative to the total weight of the composition.

The compounds of formula (I) according to the invention also find an application in the cosmetics field, in particular, for body or hair hygiene and especially for treating skin types with a tendency towards acne, for promoting the regrowth of hair, for combating hair loss, for controlling the greasy appearance of the skin or the hair, in protecting against the harmful effects of sunlight or in the treatment of physiologically dry skin types, and for preventing and/or combating light-induced or chronologic aging.

In the cosmetics field, the compounds according to the invention may also advantageously be employed in combination with other compounds having retinoid-type activity, with D vitamins or derivatives thereof, with corticosteroids, with anti-free-radical agents, α-hydroxy or α-keto acids or derivatives thereof, or alternatively with ion-channel blockers, all of these different products being as defined above or having an art-recognized definition.

The present invention is thus also directed to a cosmetic composition which comprises, in a cosmetically acceptable support or carrier which is suitable for topical application, at least one compound of formula (I) as defined above, or one of the optical or geometrical isomers thereof or one of the salts thereof. The cosmetic composition is preferably in the form of a cream, a milk, a lotion, a gel, microspheres or nanospheres or polymeric or lipid vesicles, a soap or a shampoo.

The concentration of compound of formula (I) in the cosmetic composition according to the present invention preferably ranges from 0.001% to 3% by weight relative to the composition as a whole.

The medicinal and cosmetic compositions according to the invention may also contain inert additives or even pharmacodynamically or cosmetically active additives or combinations of these additives and, in particular, wetting agents; depigmenting agents such as hydroquinone, azelaic acid, caffeic acid or kojic acid; emollients; moisturizing agents such as glycerol, PEG 400, thiamorpholinone and derivatives thereof, or, alternatively, urea; anti-seborrhea or anti-acne agents such as S-carboxymethylcysteine, S-benzylcysteamine, the salts and the derivatives thereof, or benzoyl peroxide; antibiotics such as erythromycin and esters thereof, neomycin, clindamycin and esters thereof, and tetracyclines; anti-fungal agents such as ketoconazole or 4,5-polymethylene-3-isothiazolidones; agents for promoting the regrowth of hair, such as minoxidil (2,4-diamino-6-piperidinopyrimidine 3-oxide) and derivatives thereof, diazoxide (7-chloro-3-methyl-1,2,4-benzothiadiazine 1,1-dioxide) and phenytoin (5,4-diphenylimidazolidine-2,4-dione); non-steroidal anti-inflammatory agents; carotenoids and, in particular, β-carotene; anti-psoriatic agents such as anthraline and derivatives thereof and, lastly, eicosa-5,8,11,14-tetraynoic acid and eicosa-5,8,11-trynoic acid, the esters and the amides thereof.

The compositions according to the invention may also contain flavor enhancing agents, preservatives such as parahydroxybenzoic acid esters, stabilizing agents, moisture regulators, pH regulators, osmotic pressure modifiers, emulsifying agents, UV-A and UV-B screening agents, and antioxidants such as α-tocopherol, butylhydroxyanisole or, butylhydroxytoluene.

In order to further illustrate the present invention and the advantages thereof, the following specific examples of the production of active compounds of formula (I) according to the invention, as well as various solid formulations based on such compounds are given, it being understood that same are intended only as illustrative and in nowise limitative.

A. EXAMPLES OF COMPOUNDS

EXAMPLE 1

Ethyl 4-[(E)-2-(3-(1-adamantyl)-4-methoxyethoxymethoxhenyl)ethenyl]benzoate (a) 3-(1-Adamantyl)-1-bromo-4-methoxyethoxymethoxybenzene.

3.8 g (0.13 mol) of sodium hydride (80% in oil) and 50 ml of DMF were introduced into a three-necked flask under a stream of nitrogen. A solution of 40.0 g (0.13 mol) of 2-(1-adamantyl)-4-bromophenol dissolved in 100 ml of DMF was added dropwise and the mixture was stirred until the evolution of gas had ceased. A solution of 18 ml (0.15 mol) of 2-methoxy-ethoxymethyl chloride in 20 ml of DMF was then added dropwise and the mixture was stirred for four hours at room temperature. The reaction medium was poured into water and extracted with ethyl ether. The organic phase was separated out after settling had taken place, washed with water, dried over magnesium sulfate and evaporated. The residue was purified by chromatography on a column of silica eluted with a mixture of dichloromethane and hexane (50/50). After evaporation of the solvents, 40.1 g (78%) of the expected product, with a melting point of 69–70° C., was collected.

(b) 3-(1-Adamantyl)-4-methoxyethoxymethoxyphenyl-carboxaldehyde.

34.0 g (89.0 mmol) of 3-(1-adamantyl)-1-bromo-4-methoxyethoxymethoxybenzene and 250 ml of THF were introduced into a three-necked flask under a stream of nitrogen. 43 ml (106 mmol) of a solution of n-butyllithium (2.5M in hexane) was added dropwise at −78° C. and the mixture was stirred for 30 minutes. 8.3 ml (106 mmol) of DMF was then added dropwise and the mixture was allowed to warm to room temperature. The reaction medium was poured into an aqueous ammonium chloride solution and extracted with ethyl ether. The organic phase was separated out after settling had taken place, dried over magnesium sulfate and evaporated. The residue obtained was purified by chromatography on a column of silica eluted with dichloromethane. After evaporation of the solvents, 17.6 g (58%) of the expected aldehyde, with a melting point of 63–64° C., was collected.

(c) Ethyl 4-[(E)-2-(3-(1-adamantyl)-4-methoxyethoxymethoxyphenyl)ethenyl]benzoate.

360 mg (12 mmol) of sodium hydride (80% in oil) and 20 ml of THF were introduced into a three-necked flask under a stream of nitrogen. A solution of 70 ml of THF containing 3.44 g (10 mmol) of 3-(1-adamantyl)-4-methoxyethoxymethoxyphenylcarbox-aldehyde, 3.6 g (12 mmol) of diethyl 4-ethoxycarbonyl-benzylphosphonate and 440 mg of crown ether (15-crown-5) were added dropwise. The reaction medium was stirred at room temperature for four hours and was then poured into water and extracted with ethyl ether. The organic phase was separated out after settling has taken place, dried over magnesium sulfate and evaporated. The residue obtained was triturated from hexane, filtered and dried. 4.55 g (93%) of the expected ethyl ester, with a melting point of 87–88° C., was collected.

EXAMPLE 2

4-[(E)-2-(3-(1-Adamantyl)-4-methoxy-ethoxymethoxy-phenyl) ethenyl]benzoic acid 2.0 g (4.0 mmol) of ethyl 4-[(E)-2-[3-(1-adamantyl)-4-methoxyethoxymethoxyphenyl)ethenyl]-benzoate and methanolic sodium hydroxide solution (1.6 g of sodium hydroxide in 50 ml of methanol) were introduced into a round-bottomed flask. The mixture was refluxed for four hours and evaporated to dryness, and the residue was taken up in water and acidified to pH 1. The aqueous phase was extracted with ethyl acetate and the organic phase was separated out after settling had taken place, dried over magnesium sulfate and evaporated. The residue obtained was triturated from the minimum amount of ethyl ether, filtered and dried. 1.4 g (74%) of the expected acid, with a melting point of 207–208° C., was collected.

EXAMPLE 3

Ethyl 4-[(E)-2-(3-(1-adamantyl)-4-methoxyethoxy-methoxyphenyl)-1-propenyl]benzoate (a)  3-(1-Adamantyl)-4-methoxyethoxymethoxybenzoic acid.

3-(1-Adamantyl)-1-bromo-4-methoxyethoxy-methoxybenzene (28.5 g, 72 mmol) was dissolved in 200 ml of THF. The solution obtained was added dropwise onto magnesium (2.4 g, 100 mmol) and a crystal of iodine. After introduction, the mixture was refluxed for two hours, cooled to –78° C. and a stream of $CO_2$ was passed through for one hour. The reaction medium was allowed to warm to room temperature and was then poured into saturated aqueous ammonium chloride solution and extracted with ethyl ether. The organic phase was separated out after settling had taken place, dried over magnesium sulfate and evaporated. The residue obtained was triturated from hexane, filtered and dried. 15.5 g. (60%) of the expected acid, with a melting point of 115–116° C., was collected.

(b)  3-(1-Adamantyl)-4-methoxyethoxymethoxyacetophenone.

15.5 g (43 mmol) of 3-(1-adamantyl)-4-methoxy-ethoxymethoxybenzoic acid and 300 ml of anhydrous ethyl ether were introduced into a three-necked flask under a stream of nitrogen. 80 ml (0.13 mol) of methyl]ithium (1.6M in ether) was added dropwise at –20° C. and the mixture.was then stirred at room.temperature for three hours. The reaction medium was poured into saturated aqueous ammonium chloride solution and the organic phase was separated out after settling had taken place, dried over magnesium sulfate and evaporated. 15.4 g (100%) of the expected acetophenone was collected in the form of a pale yellow oil.

(c)  Ethyl 4-[(E)-2-(3-(1-adamantyl)-4-methoxyethoxy-methoxyphenyl)-1-propenyl]benzoate.

In a similar manner to Example 1(c), by reaction of 3.58 g (10 mmol) of 3-(1-adamantyl)-4-methoxyethoxymethoxy-acetophenone with 3.13 g (12 mmol) of diethyl 4-ethoxy-carbonylbenzylphosphonate, and after chromatography on a column of silica eluted with a mixture of heptane and ethyl acetate (90/10), 2.5 g (50%) of ethyl ester was obtained in the form of a mixture of (E) and (Z) isomers.

EXAMPLE 4

4-[(E)-2-(3-(1-Adamantyl)-4-methoxy-ethoxymethoxy-phenyl)-1-propenyl]benzoic acid In a similar manner to Example 2, starting with 2.5 g (5 mmol) of an (E/Z) mixture of ethyl 4-[2-(3-(1-adamantyl)-4-methoxyethoxymethoxyphenyl)-1-propenyl]benzoate and after recrystallization from ethanol, 150 mg (13%) of 4-[(E)-2-(3-(1-adamantyl)-4-methoxyethoxymethoxyphenyl)-1-propenyl]benzoic acid, with a melting point of 177–178° C., was collected.

EXAMPLE 5

4-[(Z)-2-(3-(1-Adamantyl)-4-methoxy-ethoxymethoxy-phenyl)-1-prorenyl]benzoic acid The recrystallization filtrate obtained in Example 4 was evaporated to dryness. The solid obtained was recrystallized from ethanol and, after filtration, 140 mg (12%) of 4-[(Z)-2-(3-(1-adamantyl)-4-methoxy-ethoxymethoxyphenyl)-1-propenyl]benzoic acid, with a melting point of 198–199° C., was collected.

EXAMPLE 6

Methyl 5-{2-[3-adamant-1-yl-4-(2-methoxyethoxy-methoxy)phenyl]propen-(E)-yl}pyridine-2-carboxy-late (a) 2-Bromo-5-methylpyridine.

500 ml of aqueous hydrobromic acid (47%) was mixed with 50.0 g (462 mmol) of 2-amino-5-methyl-pyridine in a two-liter reactor. The solution obtained was cooled to –20° C. and 206.9 g (1.3 mol) of bromine was then run in over ten minutes, while keeping the temperature between –15° C. and –25° C. The reaction medium was stirred for one hour at –20° C., after which a solution composed of 82.7 g (1.2 mol) of sodium nitrite dissolved in 300 ml of water was run in dropwise over twenty minutes.

The reaction medium was stirred for four hours at room temperature and was then cooled to –10° C., 800 ml of aqueous sodium hydroxide solution (pH 10) was added and the mixture was stirred for five minutes and extracted with ethyl ether. The organic phase was separated out after settling had taken place, washed with water and then with $Na_2S_2O_3$ solution, dried over magnesium sulfate and evaporated. 75.2 g (94%) of the expected compound was collected in the form of orange crystals with a melting point of 38–42° C.

(b) 2-Bromo-5-bromomethylpyridine.

10.0 g (58.0 mmol) of the bromo compound obtained in Example 4(a) and 70 ml of carbon tetrachloride were mixed together in a 250 ml three-necked flask. The mixture was heated to about 35° C. and a ground mixture composed of 10.32 g (58.0 mmol) of N-bromosuccinimide and 421 mg (1.74 mmol) of benzoyl peroxide were introduced in a single portion. The reaction medium was refluxed under light irradiation (1000 W) for three hours. The mixture was cooled and filtered, the filtrate was evaporated to dryness, the residue was taken up in dichloromethane and washed with saturated sodium bicarbonate solution and the organic phase was then dried over magnesium sulfate and evaporated. The residue obtained was purified by chromatography on a column-of silica eluted with a mixture composed of dichloromethane and heptane (1/1). After evaporation of the solvents, 2.9 g (20%) of the expected compound was collected in the form of beige-colored crystals.

(c) Diethyl (6-bromopyrid-3-ylmethyl)phosphonate.

3.0 g (11.9 mmol) of the compound obtained in Example 6(b) and 10 ml of triethyl phosphite were mixed together in a 100 ml round-bottomed flask. The mixture was refluxed for thirty minutes, cooled and evaporated to dryness. The residue obtained was purified by chromatography on a column of silica eluted with a mixture of ethyl acetate and heptane (6/4). After evaporation of the solvents, 3.12 g (80%) of the expected compound was collected in the form of a pale yellow oil.

(d) 5-{2-[3-Adamant-1-yl-4-(2-methoxyethoxymethoxy)-phenyl]propen-(E)-yl}-2-bromopyridine.

2.6 g (8.4 mmol) of the compound obtained in Example 6(c), 5 ml of DMPU and 5 ml of THF were mixed together in a 100 ml round-bottomed flask. 250 mg (8.4 mmol) of 80% sodium hydride were added in a single portion and the mixture was stirred at room temperature for thirty minutes and then at 40° C. for fifteen minutes. A solution of 2.5 g (7.0 mmol) of the ketone obtained in Example 3(b) dissolved in 10 ml of THF was added dropwise. The reaction medium was stirred for four hours at room temperature, after which saturated citric acid solution was added. The mixture was extracted with ethyl ether and the organic phase was separated out after settling had taken place, washed with water, dried over magnesium sulfate and evaporated. The residue obtained was purified by chromatography on a column of silica eluted with a mixture of ethyl acetate and heptane (2/8). 2.69 g (75%) of the expected compound was collected in the form of a yellow oil.

(e) Methyl 5-{2-[3-adamant-1-yl-4-(2-methoxyethoxymethoxy)phenyl]propen-(E)/(Z)-yl}pyridine-2-carboxylate.

4.1 g (8.0 mmol) of the bromo compound obtained in Example 6(d), 890 mg (1.6 mmol) of 1,1'-bis(diphenylphosphino)ferrocene, 180 mg (0.8 mmol) of palladium acetate, 20 ml of DMF, 2.23 ml (16.0 mmol) of triethylamine and 3.24 ml (80 mmol) of methanol were introduced into a hydrogenation bomb. The reaction medium was confined under a pressure of three bar of carbon monoxide and heated at 100° C. for three hours. The mixture was cooled, taken up in water, extracted with ethyl acetate and washed with water. The organic phase was then dried over magnesium sulfate and evaporated. The residue obtained was purified by chromatography on a column of silica eluted with a mixture of ethyl acetate and heptane (2/8). After evaporation of the solvents, 1.3 g (33%) of the (Z) isomer in the form of a yellow oil and 1.16 g (29%) of the (E) isomer in the form of a pale yellow powder with a melting point of 96–102° C. were collected.

EXAMPLE 7

5-{2-[3-Adamant-1-yl-4-(2-methoxyethoxymethoxy)-phenyl]proxpen-(E)-yl}pyridine-2-carboxylic acid In a similar manner to Example 2, starting with 1.16 g (2.36 mmol) of the (E) isomer of methyl 5-{2-[3-adamant-1-yl-4-(2-methoxyethoxymethoxy)phenyl]-propen-yl}pyridine-2-carboxylate obtained in Example 6(e), and after purification by trituration from a mixture of ethyl ether and heptane (5/5), 0.98 g (86%) of 5-{2-[3-adamant-1-yl-4-(2-methoxyethoxymethoxy)-phenyl]propen-(E)-yl}pyridine-2-carboxylic acid was collected in the form of a beige-colored powder with a melting point of 91–95° C.

EXAMPLE 8

5-{2-[3-Adamant-1-yl-4-(2-methoxyethoxymethoxy)-phenyl]prorpen-(Z)-yl}pyridine-2-carboxylic acid In a similar manner to Example 2, starting with 1.30 g (2.64 mmol) of the (Z) isomer of methyl 5-{2-[3-adamant-1-yl-4-(2-methoxyethoxymethoxy)phenyl]-propen-yl}pyridine-2-carboxylate obtained in Example 6(e), and after trituration from heptane, 1.05 g (83%) of 5-{2-[3-adamant-1-yl-4-(2-methoxyethoxymethoxy)-phenyl]propen-(Z)-yl}pyridine-2-carboxylic acid was collected in the form of a white powder with a melting point of 91–95° C.

EXAMPLE 9

Ethyl 6-{2-[3-adamant-1-yl-4-(2-methoxyethoxymethoxy)-phenyl]propen-(E)-yl}nicotinate (a) Ethyl 6-hydroxymethylnicotinate.

45.77 g (205 mmol) of ethyl 2,5-pyridine-dicarboxylate was dissolved in 410 ml of absolute ethanol in a one-liter round-bottomed flask. The reaction medium was cooled to −5° C. and 5.04 g (133.2 mmol) of sodium borohydride was added, followed by portionwise addition of 14.79 g (133.2 mmol) of calcium chloride, while keeping the temperature below −5° C. The reaction medium was stirred at −5° C. for two hours and poured into water. The product was extracted with ethyl ether and washed with water and the organic phase was then dried over magnesium sulfate and evaporated. The residue obtained was purified by chromatography on a column of silica eluted with ethyl ether, in order to obtain 31.33 g (84%) of a white crystalline solid.

(b) Ethyl 6-bromomethylnicotinate.

10.0 g (55.2 mmol) of the compound obtained in Example 9(a), 36.6 g (110 mmol) of carbon tetrabromide and 100 ml of ethyl ether were dissolved in a 500 ml round-bottomed flask. The reaction medium was cooled to 0° C. and 40.78 g (110 mmol) of trioctylphosphine was then added over ten minutes. The reaction medium was stirred for fifteen minutes at room temperature and poured into water. The product was extracted with ethyl ether and washed with water and the organic phase was then dried over magnesium sulfate and evaporated. The residue obtained was purified by chromatography on a column of silica eluted with ethyl ether, in order to obtain 11.70 g (87%) of a red oil.

(c) Ethyl 6-(diethoxyphosphoryl)nicotinate.

11.0 g (45.0 mmol) of the compound obtained in Example 9(b) and 100 ml of triethyl phosphite were mixed together in a 100 ml round bottomed flask. The mixture was refluxed for five minutes, cooled and evaporated to dryness. The residue obtained was purified by chromatography on a column of silica eluted with a mixture of ethyl acetate and heptane (8/2). After evaporation of the solvents, 9.7 g (71%) of the expected compound was collected in the form of a yellow. oil.

(d) Ethyl 6-{2-[3-adamant-1-yl-4-(2-methoxyethoxy-methoxy)phenyl]propen-(E)-yl}nicotinate.

0.5 g (1.66 mmol) of the compound obtained in Example 9(c), 5 ml of DMPU and 5 ml of THF were mixed together in a 50 ml round-bottomed flask. 50 mg (1.66 mmol) of 80% sodium hydride was added in a single portion and the mixture was stirred at room temperature for fifteen minutes and then at 40° C. for an additional fifteen minutes. A solution of 496 mg (1.4 mmol) of the ketone obtained in Example 3(b) dissolved in 5 ml of THF is added dropwise. The reaction medium was stirred for four hours at room temperature, saturated citric acid solution was then added. The mixture was extracted with ethyl ether and the organic phase was separated out after settling had taken place, washed with water, dried over magnesium sulfate and evaporated. The residue obtained was purified by chromatography on a column of silica eluted with a mixture of ethyl acetate and heptane (2/8). 60 mg (7%) of the expected (E) compound was collected in the form of a yellow solid with a melting point of 78° C., along with a fraction corresponding to the (Z) compound, which would be directly reacted in order to obtain the corresponding acid (Example 11).

EXAMPLE 10

6-{2-[3-Adamant-1-yl-4-(2-methoxy-ethoxymethoxy)-phenyl]proven-(E)-yl}nicotinic acid In a similar manner to Example 2, starting with 1.30 g (2.57 mmol) of the (E) isomer of ethyl 6-{2-[3-adamant-1-yl-4-(2-methoxyethoxymethoxy)-phenyl]propen-yl}nicotinate obtained in Example 9(d), and after purification by chromatography on a column of silica eluted with a mixture of ethyl acetate and heptane (5/5), 0.98 g (80%) of the expected compound was collected in the form of an-off-white powder with a melting point of 86–90° C.

EXAMPLE 11

6-{2-[3-Adamant-1-yl-4-(2-methoxy-ethoxymethoxy)-phenyl]propen-(Z)-yl}nicotinic acid In a similar manner to Example 2, starting with 463 mg (0.92 mmol) of the (Z) isomer of ethyl 6-{2-[3-adamant-1-yl-4-(2-methoxyethoxymethoxy)-phenyl]propenyl}nicotinate obtained in Example 9(d), and after crystallization from a mixture of ethyl ether and heptane (5/5), 350 mg (80%) of the expected compound was collected in the form of an off-white powder with a melting point of 191–195° C.

EXAMPLE 12

Methyl 4-{2-[3-adamant-1-yl-4-(2-methoxyethoxymethoxy)phenyl]proren-(Z)-yl}-2-methoxybenzoate In a similar manner to Example 6(d), starting with 13.96 g (50.9 mmol) of diethyl 4-methoxycarbonyl-benzylphosphonate and 9.13 g (25.45 mmol) of the ketone obtained in Example 3(b), 8.25 g (62%) of the (Z) compound in the form of a white crystalline solid and 3.00 g (23%) of the (Z) compound in the form of a colorless oil were collected.

EXAMPLE 13

4-{2-[3-Adamant-1-yl-4-(2-methoxy-ethoxymethoxy)-phenyl]propen-(E)-yl}-2-methoxybenzoic acid In a similar manner to Example 2, starting with 3.00 g (5.76 mmol) of the (E) isomer of methyl 4-{2-[3-adamant-1-yl-4-(2-methoxyethoxymethoxy)phenyl]-propen-yl}-2-methoxybenzoate obtained in.Example 12, and after crystallization from methanol, 2.80 g (96%) of the expected compound was collected in the form of yellow crystals.

EXAMPLE 14

4-{2-[3-Adamant-1-yl-4-(2-methoxy-ethoxymethoxy)-phenyl]propen-(Z)-yl}-2-methoxybenzoic acid In a similar manner to Example 2, starting with 7.60 g (14.6 mmol) of the (Z) isomer of methyl 4-{2-[3-adamant-1-yl-4-(2-methoxyethoxymethoxy)-phenyl]propen-yl}-2-methoxybenzoate obtained in Example 12, and after crystallization from a mixture of ethyl ether and hexane (10/90), 7.39 g (100%) of the expected compound was collected in the form of white crystals with a melting point of 113° C.

EXAMPLE 15

Ethyl 4-{2-[3-adamant-1-yl-4-(3-ethoxymethoxypropyl)-phenyl]propen-(E/Z)-yl}benzoate (a) Methyl 3-adamant-1-yl-4-trifluoromethane-sulphonyloxybenzoate.

28.6 g (100.0 mmol) of methyl 3-(1-adamantyl)-4-hydroxybenzoate was mixed with 122 mg (1.0 mmol) of N,N-dimethylaminopyridine, 200 ml of dichloromethane and 28 ml of pyridine in a one liter three-necked flask under a nitrogen atmosphere. The mixture was cooled to −78° C. and 20.19 ml (120.0 mmol) of triflic anhydride was added dropwise. The temperature was raised to room temperature and the mixture was continuously stirred for two hours. The reaction medium was poured into 1N hydrochloric acid solution, extracted with ethyl ether, washed with water, dried over magnesium sulfate, filtered and evaporated to dryness. 41.5 g (99%) of the expected compound was collected in the form of a pale orange powder-with a melting point of 95° C.

(b) Methyl 3-adamant-1-yl-4-allylbenzoate.

23.06 g (55.1 mmol) of the compound obtained in Example 15(a) was mixed with 4.66 g (110.0 mmol) of lithium chloride, 5.8 g (8.3 mmol) of bis(triphenylphosphine)palladium(II) chloride, 21.89 g (66.0 mmol) of allyl-tributyltin and 300 ml of N,N-dimethylformamide in a one liter three-necked flask under a nitrogen atmosphere. The mixture was heated at 100° C. for two hours and was then poured into 1N hydrochloric acid solution, extracted with ethyl ether, washed with water, dried over magnesium sulfate, filtered and evaporated to dryness. The residue obtained was purified by distillation of tin salts (108–116° C. at $8 \cdot 10^{-2}$ bar) followed by chromatography on a column of silica eluted with heptane. After evaporation of the solvents, 12.75 g (74%) of the expected compound was collected in the form of a yellow oil.

(c) Methyl 3-adamant-1-yl-4-(3-hydroxypropyl)benzoate.

12.40 g (40.0 mmol) of the compound obtained in Example 15(b) was dissolved in 250 ml of tetrahydrofuran in a 250 ml three-necked flask under a nitrogen atmosphere. The mixture was cooled to 0° C. and 240 ml (120.0 mmol) of 9-borabicyclo[3.3.1]nonane (9-BBN) was then run in dropwise and the mixture was stirred at room temperature for two hours. The reaction medium was again cooled to 0° C. and 124 ml (124 mmol) of aqueous sodium hydroxide solution (1M) was then run in dropwise, followed, while maintained at 0° C., by 102 ml (1 mol) of 30% aqueous hydrogen peroxide solution. The reaction medium was stirred for thirty minutes at room temperature and was then poured into 1N hydrochloric acid solution, extracted-with ethyl ether, washed with water, dried over magnesium sulfate, filtered and evaporated to dryness. The residue was purified by chromatography on a column of silica eluted with a mixture composed of 30% ethyl acetate and 70% heptane. 9.4 g (71%) of the expected compound were collected in the form of a white powder with a melting point of 77° C.

(d) Methyl 3-adamant-1-yl-4-(3-ethoxymethoxypropyl)-benzoate.

8.00 g (24.3 mmol) of the compound obtained in Example 15(c) was dissolved in 200 ml of toluene in a 500 ml three-necked flask under a nitrogen atmosphere. 577 mg (1.7 mmol) of tetrabutylamine hydrogen sulfate was added, the mixture was cooled to 0° C. and 6.78 ml (73.0 mmol) of ethoxymethyl chloride and 120 ml of aqueous 10 M sodium hydroxide were then run in dropwise. The reaction medium was stirred at 0° C. for thirty minutes and then poured into 1N hydrochloric acid solution, extracted with ethyl ether, washed with water, dried over magnesium sulfate, filtered and evaporated to dryness. 9.39 g (100%) of the expected compound were collected in the form of a pale yellow oil.

(e) 3-Adamant-1-yl-4-(3-ethoxymethoxypropyl)benzoic acid.

In a similar manner to Example 2, starting with 9.39 g (24.3 mmol) of the compound obtained in Example 15(d), 8.52 g (94%) of the expected compound was collected in the form of a white powder with a melting point of 115° C.

(f) 1-[3-Adamant-1-yl-4-(3-ethoxymethoxypropyl)phenyl]-ethanone.

In a similar manner to Example 3(b), starting with 8.00 g (21.5 mmol) of the compound obtained in Example 15(e), 5.34 g (67%) of the expected compound was collected in the form of a colorless oil.

(g) Ethyl 4-{2-[3-adamant-1-yl-4-(3-ethoxymethoxy-propyl)phenyl]propen-(E/Z)-yl}benzoate.

In a similar manner to Example 1(c), by reaction of 5.00 g (13.5 mmol) of the compound obtained in Example 15(f) with 8.10 g (27.0 mmol) of diethyl 4-ethoxycarbonylbenzylphosphonate, and after chromatography on a column of silica eluted with a mixture of heptane and ethyl acetate (90/10), 6.3 g (90%) of the ethyl ester was obtained in the form of a mixture of (E) and (Z) isomers.

EXAMPLE 16

4-{2-[3-Adamant-1-yl-4-(3-ethoxymethoxypropyl)-phenyl]propen-(E/Z)-yl}benzoic acids In a similar manner to Example 2, starting with 1.00 g (1.9 mmol) of the mixture of (E) and (Z) compounds obtained in Example 15(g), and after chromatography on a column of silica eluted with a mixture of heptane and ethyl acetate (80/20), 330 mg (34%) of the expected compound (Z isomer) in the form of a white powder with a melting point of 161° C., and 70 mg (7%) of the expected compound (E isomer) in the form of a white powder with a melting point of 165° C., were collected.

EXAMPLE 17

Ethyl 4-{2-[3-adamant-1-yl-4-(3-benzyloxypropyl)-phenyl]propen-(E/Z)-yl}benzoate.

(a) Ethyl 4-{2-[3-adamant-1-yl-4-(3-hydroxypropyl)-phenyl]propen-(E/Z)-yl}benzoate.

5.00 g (9.68 mmol) of the compound obtained in Example 15(g) was dissolved in 50 ml of absolute ethanol in a 250 ml three-necked flask under a nitrogen atmosphere. 5.18 ml (96.8 mmol) of concentrated sulfuric acid was added dropwise. The reaction medium was stirred at room temperature for 24 hours and then at 40° C. for 5 hours, it was poured into water, extracted with ethyl ether, washed with water, dried over magnesium sulfate, filtered and evaporated to dryness. 4.40 g (99%) of the expected compound was collected in the form of a pale yellow oil.

(b) Ethyl 4-{2-[3-adamant-1-yl-4-(3-benzyloxypropyl)-phenyl]propen-(E/Z)-yl}benzoate.

In a similar manner to Example 15(d), starting with 1.00 g (2.18 mmol) of the compound obtained in Example 17(a) and 0.78 ml (6.54 mmol) of benzyl bromide, 1.19 g (100%) of the expected compound was collected in the form of a yellow oil.

EXAMPLE 18

4-{2-[3-Adamant-1-yl-4-(3-benzyloxypropyl)phenyl]-propen-(E/Z)-yl}benzoic acids

In a similar manner to Example 2, starting with 1.00 g (1.82 mmol) of the mixture of (E) and (Z) compounds obtained in Example 17(b), and after chromatography on a column of silica eluted with a mixture of heptane and ethyl acetate (90/10), 480 mg (50%) of the expected compound (Z isomer) in the form of a white powder with a melting point of 166° C., and 175 mg (18%) of the expected compound (E isomer) in the form of a white powder with a melting point of 243° C., were collected.

EXAMPLE 19

Ethyl 4-{2-[3-adamant-1-yl-4-(3-diethylcarbamoyl-methoxyproryl)phenyl]propenyl}benzoate In a similar manner to Example 15(d), starting with 1.00 g (2.18 mmol) of the compound obtained in Example 17(a) and 0.83 ml (6.54 mmol) of N,N-diethylchloroacetamide, 1.00 g (80%) of the expected compound was collected in the form of a pale yellow oil.

EXAMPLE 20

4-{2-[3-Adamant-1-yl-4-(3-diethylcarbamoyl-methoxy-propyl)phenyl]propenyl}benzoic acid In a similar manner to Example 2, starting with 1.00 g (1.75 mmol) of the mixture of (E) and (Z) compounds obtained in Example 19(a), and after chromatography on a column of silica eluted with a mixture of heptane and ethyl acetate (90/10), 480 mg (50%) of the mixture (Z+E) of the expected compounds was collected.

EXAMPLE 21

Ethyl 4-{2-[3-adamant-1-yl-4-(3-carboxymethoxy-propyl)phenyl]propenyl}benzoate (a) Ethyl 4-{2-[3-adamant-1-yl-4-(3-tert-butoxy-carbonylmethoxypropyl)phenyl]propenyl}benzoate.

In a similar manner to Example 15(d), starting with 2.45 g (5.34 mmol) of the compound obtained in Example 17(a) and 2.59 ml (16.0 mmol) of tert-butyl bromoacetate, and after chromatography on a column of silica eluted with a mixture of heptane and ethyl acetate (90/10), 2.65 g (86%) of the mixture (Z+E) of the expected compounds was collected in the form of a colorless oil.

(b) Ethyl 4-{2-[3-adamant-1-yl-4-(3-carboxymethoxy-propyl)phenyl]propenyl}benzoate.

2.60 g (4.54 mmol) of the compound obtained in Example 21(a) was dissolved in 45 ml of dichloromethane in a 100 ml round-bottomed flask under a nitrogen atmosphere, and 3.50 ml (45.4 mmol) of trifluoroacetic acid was added dropwise. The reaction medium was stirred at room temperature for 16 hours and then at reflux for 8 hours. It was poured into water, extracted with dichloromethane, washed with water, dried over magnesium sulfate, filtered and evaporated to dryness. 2.35 g (100%) of the expected compound was collected in the form of a pale yellow oil.

EXAMPLE 22

4-{2-[3-Adamant-1-yl-4-(3-carboxymethoxypropyl)-phenyl]propenyl}benzoic acids

In a similar manner to Example 2, starting with 300 mg (0.60 mmol) of the mixture of (E) and (Z) compounds obtained in Example 21(b), and after trituration from a mixture composed of 20% ethyl ether and 80% heptane, 150 mg (51%) of the mixture (Z+E) of the expected compounds was collected.

EXAMPLE 23

Ethyl 4-{2-[3-adamant-1-yl-4-(3-carbamoyl-methoxy-propyl)phenyl]propenyl}benzoate 1.00 g (1.93 mmol) of the compound obtained in Example 21(b) was dissolved in 20 ml of dichloromethane in a 100 ml round-bottomed flask under a nitrogen atmosphere, and 0.42 ml (2.13 mmol) of dicyclohexylamine was added dropwise. The reaction medium was stirred at room temperature for five minutes, after which 0.14 ml (1.93 mmol) of thionyl chloride was added dropwise and the mixture was stirred at room temperature for twenty minutes. The reaction medium was evaporated to dryness, taken up in ethyl ether and filtered and the filtrate was evaporated in order to obtain a yellow oil which was taken up in 10 ml of THF in order to obtain a solution. This solution was added dropwise to a solution composed of 0.13 ml of 32% aqueous ammonia solution (2.13 mmol) in 20 ml of THF and 0.32 ml (2.32 mmol) of triethylamine. The reaction medium was stirred at room temperature for five minutes, poured into water and the pH was adjusted to 2 by addition of 0.5N HCl. The product was extracted with ethyl ether, washed with water, dried over magnesium sulfate, filtered and evaporated to dryness. After chromatography on a column of silica eluted with a mixture of heptane and ethyl acetate (50/50), 650 mg (65%) of the mixture (Z+E) of the expected compounds was collected.

EXAMPLE 24

4-{2-[3-Adamant-1-yl-4-(3-carbamoylmethoxypropyl)-phenyl]propenyl}benzoic acids

In a similar manner to Example 2, starting with 650 mg (1.26 mmol) of the mixture of (E) and (Z) compounds obtained in Example 23, and after trituration from admixture composed of 20% ethyl ether and 80% heptane, 340 mg (55%) of the mixture (Z+E) of the expected compounds was collected.

EXAMPLE 25

The antagonist activity of the compounds of formula (I) was evaluated in the mouse embryonic teratocarcinoma F9 cell differentiation test, (*Cancer Research,* 43, 5268 (1983)).

These compounds tested at $10^{-6}$ M were inactive as agonists in this test and partially or totally inhibit the effect produced by an agonist retinoid on the morphology and secretion of the plasminogen activator, according to the following procedure.

The F9 cells were inoculated in 12-well clusters, the compounds were tested at from $10^{-9}$ to $10^{-5}$ M in the presence of all-trans-retinoic acid or of a synthetic agonist retinoid, 4-(5,6,7,8-tetrahydro-5,5,8,8-tetramethyl-2-naphthylaminomethyl)benzoic acid (CD 2043), at $10^{-8}$ M. After incubation for three days, the morphological observations were carried out and the concentration of the test compound which inhibits the agonist effect on the secretion of the plasminogen activator by 50% (IC50) was determined.

| Example No. | Antagonist against CD 2043 (10 nM) F9 differentiation test IC50 (nM) |
|---|---|
| 2 | 310 |
| 4 | 9 |
| 5 | 630 |
| 10 | 35 |
| 7 | 600 |

B. FORMULATION EXAMPLES (1) Oral Route (a) The Following Composition was Prepared in the Form of a 0.8 g Tablet:

| | |
|---|---|
| Compound of Example 1 | 0.005 g |
| Pregelatinized starch | 0.265 g |
| Microcrystalline cellulose | 0.300 g |
| Lactose | 0.200 g |
| Magnesium stearate | 0.030 g |

For the treatment of acne, 1 to 3 tablets will be administered to an adult individual each day for 3 to 6 months depending on the severity of the case being treated.

(b) A drinkable Suspension Intended to be Packaged in 5 ml Ampules is Prepared:

| | |
|---|---|
| Compound of Example 2 | 0.050 g |
| Glycerol | 0.500 g |
| 70% Sorbitol | 0.500 g |
| Sodium saccharinate | 0.010 g |
| Methyl parahydroxybenzoate | 0.040 g |
| Flavoring qs | |
| Purified water qs | 5 ml |

For the treatment of acne, 1 ampule will be administered to an adult individual each day for 3 months depending on the severity of the case being treated.

| | |
|---|---|
| Compound of Example 4 | 0.025 g |
| Corn starch | 0.060 g |
| Lactose qs | 0.300 g |

The gelatin capsules used consist of gelatin, titanium oxide and a preservative. In the treatment of psoriasis, 1 gelatin capsule will be administered to an adult individual each day for 30 days.

2) Topical Route (a) The Following Nonionic Water-in-Oil Cream is Prepared:

| | |
|---|---|
| Compound of Example 1 | 0.100 g |
| Mixture of emulsifying lanolin alcohols, waxes and refined oils, having the trademark "Anhydrous Eucerin", by BDF | 39.900 g |
| Methyl para-hydroxybenzoate | 0.075 g |
| Propyl para-hydroxybenzoate | 0.075 g |
| Sterile demineralized water qs | 100.000 g |

This cream will be applied to psoriatic skin once or twice a day for 30 days.

(b) A Gel is Prepared by Making the Following Formulation:

| | |
|---|---|
| Compound of Example 3 | 0.050 g |
| Base erythromycin | 4.000 g |
| Butylhydroxytoluene | 0.050 g |
| Hydroxypropylcellulose having the trademark "Klucel HF" by Hercules | 2.000 g |
| Ethanol (95%) qs | 100.000 g |

This gel will be applied to skin affected with dermatitis or to acneic skin 1 to 3 times each day for 6 to 12 weeks depending on the severity of the case being treated.

(c) An Antiseborrheic Lotion is Prepared by Mixing Together the Following Ingredients:

| | |
|---|---|
| Compound of Example | 20.030 g |
| Propylene glycol | 5.000 g |
| Butylhydroxytoluene | 0.100 g |
| Ethanol (95%) qs | 100.000 g |

This lotion will be applied twice each day to a seborrheic scalp and a significant improvement is observed within a period of 2 to 6 weeks.

(d) A Cosmetic Composition to Combat the Harmful Effects of the Sun is Prepared by Mixing Together the Following Ingredients:

| | |
|---|---|
| Compound of Example 12 | 1.000 g |
| Benzylidene camphor | 4.000 g |
| Fatty acid triglycerides | 31.000 g |
| Glyceryl monostearate | 6.000 g |

| | |
|---|---|
| Stearic acid | 2.000 g |
| Cetyl alcohol | 1.200 g |
| Lanolin | 4.000 g |
| Preservative | 0.300 g |
| Propylene glycol | 2.000 g |
| Triethanolamine | 0.500 g |
| Fragrance | 0.400 g |
| Demineralized water qs | 100.000 g |

This composition will be applied daily and makes it possible to combat light-induced aging.

(e) The Following Nonionic Oil-in-Water Cream is Prepared:

| | |
|---|---|
| Compound of Example 14 | 0.500 g |
| Vitamin D3 | 0.020 g |
| Cetyl alcohol | 4.000 g |
| Glyceryl monostearate | 2.500 g |
| PEG 50 stearate | 2.500 g |
| Karite butter | 9.200 g |
| Propylene glycol | 2.000 g |
| Methyl parahydroxybenzoate | 0.075 g |
| Propyl parahydroxybenzoate | 0.075 g |
| Sterile demineralized water qs | 100.000 g |

This cream will be applied to psoriatic skin once or twice each day for 30 days.

(f) A Topical Gel is Prepared by Mixing Together the Following Ingredients:

| | |
|---|---|
| Compound of Example 18 | 0.050 g |
| Ethanol | 43.000 g |
| α-Tocopherol | 0.050 g |
| Carboxyvinyl polymer, trademark "Carbopol 941" by Goodrich | 0.500 g |
| Triethanolamine as an aqueous solution containing 20% by weight | 3.800 g |
| Water | 9.300 g |
| Propylene glycol qs | 100.000 g |

This gel will be applied in the treatment of acne 1 to 3 times each day for 6 to 12 weeks depending on the severity of the case being treated.

(g) A Lotion for Preventing Hair Loss and for Promoting Hair Regrowth is Prepared by Mixing Together the Following Ingredients:

| | |
|---|---|
| Compound of Example 15 | 0.05 g |
| Minoxidil | 1.00 g |
| Propylene glycol | 20.00 g |
| Ethanol | 34.92 g |
| Polyethylene glycol having a molecular weight of 400 | 40.00 g |
| Butylhydroxyanisole | 0.01 g |
| Butylhydroxytoluene | 0.02 g |
| Water qs | 100.00 g |

This lotion will be applied twice a day for 3 months to a scalp which has lost a considerable amount of hair.

(h) An Anti-Acne Cream is Prepared by Mixing Together the Following Ingredients:

| | |
|---|---|
| Compound of Example 5 | 0.050 g |
| Retinoic acid | 0.010 g |
| Mixture of glyceryl stearates and polyethylene glycol (75 mol), having the trademark "Gelot 64" by Gattefosse | 15.000 g |
| Polyoxyethylenated kernel oil containing 6 mol of ethylene oxide, having the trademark "Labrafil M2130 CS" by Gattefosse | 8.000 g |
| Perhydrosqualene | 10.000 g |
| Preservatives | qs |
| Polyethylene glycol having a molecular weight of 400 | 8.000 g |
| Disodium salt of ethylenediaminetetra-acetic acid | 0.050 g |
| Purified water qs | 100.000 g |

This cream will be applied to skin affected with dermatitis or to acneic skin 1 to 3 times each day for 6 to 12 weeks.

(i) An Oil-in-Water Cream is Prepared by Making the Following Formulation:

| | |
|---|---|
| Compound of Example 20 | 0.020 g |
| Betamethasone 17-valerate | 0.050 g |
| S-Carboxymethylcysteine | 3.000 g |
| Polyoxyethylene stearate (40 mol of ethylene oxide) having the trademark "Myrj 52" by Atlas | 4.000 g |
| Sorbitan monolaurate polyoxyethylenated with 20 mol of ethylene oxide, having the trademark "Tween 20" by Atlas | 1.800 g |
| Mixture of glyceryl mono- and distearate, having the trademark "Géléol" by Gattefosse | 4.200 g |
| Propylene glycol | 10.000 g |
| Butylhydroxyanisole | 0.010 g |
| Butylhydroxytoluene | 0.020 g |
| Cetostearyl alcohol | 6.200 g |
| Preservatives | qs |
| Perhydrosqualene | 18.000 g |
| Mixture of caprylic/capric triglycerides, having the trademark "Miglyol 812" by Dynamit Nobel | 4.000 g |
| Triethanolamine (99% by weight) | 2.500 g |
| Water qs | 100.000 g |

This cream will be applied twice a day to skin affected with dermatitis, for 30 days.

(j) The Following Cream of Oil-in-Water Type is Prepared:

| | |
|---|---|
| Lactic acid | 5.000 g |
| Compound of Example 23 | 0.020 g |
| Polyoxyethylene stearate (40 mol of ethylene oxide), having the trademark "Myrj 52" by Atlas | 4.000 g |
| Sorbitan monolaurate polyoxyethylenated with 20 mol of ethylene oxide, having the trademark "Tween 20" by Atlas | 1.800 g |
| Mixture of glyceryl mono- and distearate, having the trademark "Geleol" by Gattefosse | 4.200 g |
| Propylene glycol | 10.000 g |
| Butylhydroxyanisole | 0.010 g |
| Butylhydroxytoluene | 0.020 g |
| Cetostearyl alcohol | 6.200 g |
| Preservatives | qs |
| Perhydrosqualene | 18.000 g |
| Mixture of caprylic/capric triglycerides, having the trademark "Miglyol 812" by Dynamit Nobel | 4.000 g |
| Water qs | 100.000 g |

This cream will be applied once a day and helps to combat aging, both light-induced and chronologic aging.

While the invention has been described in terms of various preferred embodiments, the skilled artisan will appreciate that various modifications, substitutions, omissions, and changes may be made without departing from the spirit thereof. Accordingly, it is intended that the scope of the present invention be limited solely by the scope of the following claims, including equivalents thereof.

What is claimed is:

1. A method for the treatment of psoriasis, acne, eczema or dermatitis comprising administering an effective amount of at least one stilbene compound to a patient in need of such treatment, said at least one stilbene compound having the formula (I):

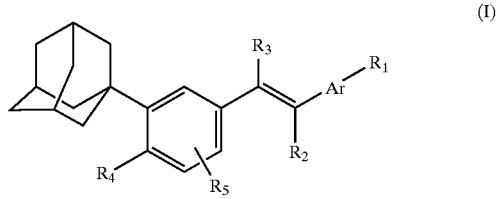

(I)

wherein:
    $R_1$ represents
        (i) the —$CH_3$ radical,
        (ii) the radical —$CH_2$—O—$R_6$,
        (iii) the radical —O—$R_6$, or
        (iv) the radical —CO—$R_7$,
        wherein the radicals $R_6$ and $R_7$ have the meanings given below,
    Ar represents a radical selected from the group consisting of one of the radicals of formulae (a) to (f):

(a)

-continued

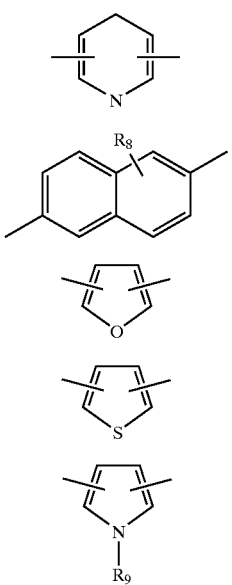

wherein $R_8$ and $R_9$ have the meanings given below, $R_2$ and $R_3$, which may be identical or different, represent a hydrogen atom or a lower alkyl radical, $R_4$ represents the radical $-(X)_m-(CH_2)_n-Y-(CH_2)_p-R_{10}$, the values m, n and p and the radicals X, Y and $R_{10}$ having the meanings given below, $R_5$ represents a hydrogen or halogen atom, a lower alkyl radical or a radical $-O-R_6$, $R_6$ represents a hydrogen atom, a lower alkyl radical or a radical $-CO-R_{11}$, $R_7$ represents a hydrogen atom, a lower alkyl radical, a radical $-OR_{12}$ or a radical

wherein R' and R", which may be identical or different, represent a hydrogen atom, a lower alkyl radical, a mono- or polyhydroxyalkyl radical, or a phenyl radical optionally substituted with a substituent selected from the group consisting of a halogen atom, a hydroxyl radical, an alkyl radical, a nitro function, a methoxy group and an optionally substituted amine function, or alternatively, taken together, R' and R" form a heterocycle, wherein m is an integer equal to 0 or 1, n is an integer ranging from 1 to 6, inclusive, p is an integer ranging from 1 to 6, inclusive, X represents O or $S(O)_q$, Y represents O or $S(O)_q$, q is an integer ranging from 0 to 2, inclusive, $R_8$ represents a hydrogen or halogen atom, a lower alkyl radical or a radical $-O-R_6$, $R_9$ represents a hydrogen atom, a lower alkyl radical or a radical $-CO-R_{11}$, $R_{10}$ represents a mono- or polyhydroxyalkyl radical wherein the hydroxyls are optionally protected in the form of methoxy, ethoxy, acetoxy or acetonide, a radical $-CO-R_7$ or a benzyl or phenethyl radical, optionally substituted with a substituent selected from the group consisting of a halogen atom, a hydroxyl, a nitro function and a methoxy group, $R_{11}$ represents a lower alkyl radical, $R_{12}$ represents a hydrogen atom, an alkyl radical, an alkenyl radical, a mono- or polyhydroxyalkyl radical in which the hydroxyls are optionally protected in the form of methoxy, ethoxy, acetoxy or acetonide, a phenyl radical optionally substituted with a substituent selected from the group consisting of a halogen atom, a hydroxyl radical, an alkyl radical, a nitro function, a methoxy group and an optionally substituted amine function, or a benzyl or phenethyl radical, optionally substituted with a substituent selected from the group consisting of a halogen atom, a hydroxyl, a nitro function and a methoxy group, or a salt thereof, or an optical or geometrical isomer thereof.

2. A method for the treatment of cutaneous psoriasis, mucous psoriasis, ungual psoriasis, psoriatic rheumatism, eczema, acne, or dermatitis comprising administering an effective amount of at least one stilbene compound to a patient in need of such treatment, said at least one stilbene compound having the formula (I):

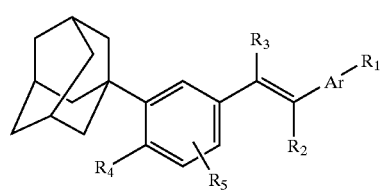

wherein:

$R_1$ represents (i) the $-CH_3$ radical, (ii) the radical $-CH_2-O-R_6$, (iii) the radical $-O-R_6$, or (iv) the radical $-CO-R_7$, wherein the radicals $R_6$ and $R_7$ have the meanings given below, Ar represents a radical selected from the group consisting of one of the radicals of formulae (a) to (f):

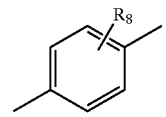

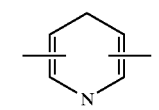

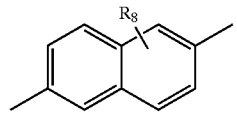

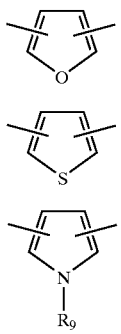

wherein $R_8$ and $R_9$ have the meanings given below,
$R_2$ and $R_3$, which may be identical or different, represent a hydrogen atom or a lower alkyl radical,
$R_4$ represents the radical $—(X)_m—(CH_2)_n—Y—(CH_2)_p—R_{10}$,
the values m, n and p and the radicals X, Y and $R_{10}$ having the meanings given below,
$R_5$ represents a hydrogen or halogen atom, a lower alkyl radical or a radical $—O—R_6$,
$R_6$ represents a hydrogen atom, a lower alkyl radical or a radical $—CO—R_{11}$,
$R_7$ represents a hydrogen atom, a lower alkyl radical, a radical $—OR_{12}$ or a radical

wherein R' and R'', which may be identical or different, represent a hydrogen atom, a lower alkyl radical, a mono- or polyhydroxyalkyl radical, or a phenyl radical optionally substituted with a substituent selected from the group consisting of a halogen atom, a hydroxyl radical, an alkyl radical, a nitro function, a methoxy group and an optionally substituted amine function, or alternatively, taken together, R' and R'' form a heterocycle,
wherein
m is an integer equal to 0 or 1,
n is an integer ranging from 1 to 6, inclusive,
p is an integer ranging from 1 to 6, inclusive,
X represents O or $S(O)_q$,
Y represents O or $S(O)_q$,
q is an integer ranging from 0 to 2, inclusive,
$R_8$ represents a hydrogen or halogen atom, a lower alkyl radical or a radical $—O—R_6$,
$R_9$ represents a hydrogen atom, a lower alkyl radical or a radical $—CO—R_{11}$,
$R_{10}$ represents a mono- or polyhydroxyalkyl radical wherein the hydroxyls are optionally protected in the form of methoxy, ethoxy, acetoxy or acetonide, a radical $—CO—R_7$ or a benzyl or phenethyl radical, optionally substituted with a substituent selected from the group consisting of a halogen atom, a hydroxyl, a nitro function and a methoxy group,
$R_{11}$ represents a lower alkyl radical,
$R_{12}$ represents a hydrogen atom, an alkyl radical, an alkenyl radical, a mono- or polyhydroxyalkyl radical in which the hydroxyls are optionally protected in the form of methoxy, ethoxy, acetoxy or acetonide, a phenyl radical optionally substituted with a substituent selected from the group consisting of a halogen atom, a hydroxyl radical, an alkyl radical, a nitro function, a methoxy group and an optionally substituted amine function, or a benzyl or phenethyl radical, optionally substituted with a substituent selected from the group consisting of a halogen atom, a hydroxyl, a nitro function and a methoxy group,
or a salt thereof, or an optical or geometrical isomer thereof.

3. A method for the treatment of psoriasis, acne, eczema or dermatitis comprising administering an effective amount of at least one stilbene compound to a patient in need of such treatment, said at least one stilbene compound being selected from the group consisting of:

Ethyl 4-[(E)-2-(3-(1-adamantyl)-4-methoxyethoxy-methoxyphenyl)ethenyl]benzoate;
4-[(E)-2-(3-(1-Adamantyl)-4-methoxyethoxymethoxyphenyl)ethenyl]benzoic acid;
Ethyl 4-[(E)-2-(3-(1-adamantyl)-4-methoxyethoxy-methoxyphenyl)-1-propenyl]benzoate;
4-[(E)-2-(3-(1-Adamantyl)-4-methoxyethoxymethoxyphenyl)-1-propenyl]benzoic acid;
4-[(Z)-2-(3-(1-Adamantyl)-4-methoxyethoxymethoxyphenyl)-1-propenyl]benzoic acid;
Methyl 5-{2-[3-adamant-1-yl-4-(2-methoxyethoxy-methoxy)phenyl]hropen-(E)-yl}pyridine-2-carboxylate;
5-{2-[3-Adamant-1-yl-4-(2-methoxyethoxymethoxy)-phenyl]propen-(E)-yl}pyridine-2-carboxylic acid;
5-{2-[3-Adamant-1-yl-4-(2-methoxyethoxymethoxy)-phenyl]propen-(Z)-yl}pyridine-2-carboxylic acid;
Ethyl 6-{2-[3-adamant-1-yl-4-(2-methoxy-ethoxymethoxy)phenyl]propen-(E)-yl}nicotinate;
6-{2-[3-Adamant-1-yl-4-(2-methoxyethoxymethoxy)-phenyl]propen-(E)-yl}nicotinic acid;
6-{2-[3-Adamant-1-yl-4-(2-methoxyethoxymethoxy)-phenyl]propen-(Z)-yl}nicotinic acid;
Methyl 4-{2-[3-adamant-1-yl-4-(2-methoxyethoxy-methoxy)phenyl]propen-(Z)-yl}-2-methoxybenzoate;
4-{2-[3-Adamant-1-yl-4-(2-methoxyethoxymethoxy)-phenyl]propen-(E)-yl-}2-methoxybenzoic acid;
4-{2-[3-Adamant-1-yl-4-(2-methoxyethoxymethoxy)-phenyl]propen-(Z)-yl}-2-methoxybenzoic acid;
Ethyl 4-{2-[3-adamant-1-yl-4-(3-methoxymethoxypropyl)phenyl]propen-(E/Z)-yl}benzoate;
4-{2-[3-Adamant-1-yl-4-(3-ethoxymethoxypropyl)phenyl]propen-(E)-yl}benzoic acid;
4-{2-[3-Adamant-1-yl-4-(3-ethoxymethoxypropyl)phenyl]propen-(Z)-yl}benzoic acid;
Ethyl 4-{2-[3-adamant-1-yl-4-(3-benzyloxypropyl)-phenyl]propen-(E/Z)-yl}-benzoate;
4-{2-[3-Adamant-1-yl-4-(3-benzyloxypropyl)phenyl]-propen-(E)-yl}-benzoic acid;
4-{2-[3-Adamant-1-yl-4-(3-benzyloxypropyl)phenyl]-propen-(Z)-yl}benzoic acid;
Ethyl 4-{2-[3-adamant-1-yl-4-(3-diethylcarbamoyl-methoxypropyl)phenyl]propenyl}benzoate;
4-{2-[3-Adamant-1-yl-4-(3-diethylcarbamoylmethoxypropyl)phenyl]propenyl}benzoic acid;
Ethyl 4-{2-[3-adamant-1-yl-4-(3-carboxymethoxy-propyl)phenyl]propenyl}benzoate;
4-{2-[3-Adamant-1-yl-4-(3-carboxymethoxypropyl)-phenyl]propenyl}benzoic acid;
Ethyl 4-{2-[3-adamant-1-yl-4-(3-carbamoylmethoxy-propyl)phenyl]propenyl}benzoate;

4-{2-[3-Adamant-1-yl-4-(3-carbamoylmethoxypropyl)-phenyl]propenyl}benzoic acid;
N-Ethyl-4-[(E)-2-(3-(1-adamantyl)-4-methoxyethoxymethoxyphenyl)-1-propenyl]benzamide;
4-[(E)-2-(3-(1-Adamantyl)-4-methoxyethoxymethoxyphenyl)-1-propenyl]benzamide;
N-4-(Hydroxyphenyl)-4-[(E)-2-(3-(1-adamantyl)-4-methoxyethoxymethoxyphenyl)-1-propenyl]benzamide;
4-[(E)-2-(3-(1-Adamantyl)-4-methoxyethoxymethoxyphenyl)-1-propenyl]benzenemethanol;
4-[(E)-2-(3-(1-Adamantyl)-4-methoxyethoxymethoxyphenyl)-1-propenyl]benzaldehyde;
4-[(E)-2-(3-(1-Adamantyl)-4-methoxyethoxymethoxyphenyl)-1-propenyl]phenol;
4-[(E)-2-(3-(1-Adamantyl)-4-methoxyethoxymethoxyphenyl)-1-propenyl]benzoic acid morpholide; and
4-[(E)-2-(3-(1-Adamantyl)-4-methoxyethoxymethyl-sulphanylphenyl)-1-propenyl]benzoic acid.

4. A method for the treatment of cutaneous psoriasis, mucous psoriasis, ungual psoriasis, psoriatic rheumatism, eczema, acne, or dermatitis comprising administering an effective amount of at least one stilbene compound to a patient in need of such treatment, said at least one stilbene compound being selected from the group consisting of:
Ethyl 4-[(E)-2-(3-(1-adamantyl)-4-methoxyethoxy-methoxyphenyl)ethenyl]benzoate;
4-[(E)-2-(3-(1-Adamantyl)-4-methoxyethoxymethoxyphenyl)ethenyl]benzoic acid;
Ethyl 4-[(E)-2-(3-(1-adamantyl)-4-methoxyethoxy-methoxyphenyl)-1-propenyl]benzoate;
4-[(E)-2-(3-(1-Adamantyl)-4-methoxyethoxymethoxyphenyl)-1-propenyl]benzoic acid;
4-[(Z)-2-(3-(1-Adamantyl)-4-methoxyethoxymethoxyphenyl)-1-propenyl]benzoic acid;
Methyl 5-{2-[3-adamant-1-yl-4-(2-methoxyethoxy-methoxy)phenyl]propen-(E)-yl}pyridine-2-carboxylate;
5-{2-[3-Adamant-1-yl-4-(2-methoxyethoxymethoxy)phenyl]propen-(E)-yl}pyridine-2-carboxylic acid;
5-{2-[3-Adamant-1-yl-4-(2-methoxyethoxymethoxy)phenyl]propen-(Z)-yl}pyridine-2-carboxylic acid;
Ethyl 6-{2-[3-adamant-1-yl-4-(2-methoxyethoxymethoxy)phenyl]propen-(E)-yl}nicotinate;
6-{2-[3-Adamant-1-yl-4-(2-methoxyethoxymethoxy)phenyl]propen-(E)-yl}nicotinic acid;
6-{2-[3-Adamant-1-yl-4-(2-methoxyethoxymethoxy)phenyl]propen-(Z)-yl}nicotinic acid;
Methyl 4-{2-[3-adamant-1-yl-4-(2-methoxyethoxy-methoxy)phenyl]propen-(Z)-yl}-2-methoxybenzoate;
4-{2-[3-Adamant-1-yl-4-(2-methoxyethoxymethoxy)phenyl]propen-(E)-yl}-2-methoxybenzoic acid;
4-{2-[3-Adamant-1-yl-4-(2-methoxyethoxymethoxy)phenyl]propen-(Z)-yl}-2-methoxybenzoic acid;
Ethyl 4-{2-[3-adamant-1-yl-4-(3-ethoxymethoxypropyl)phenyl]propen-(E/Z)-yl}benzoate;
4-{2-[3-Adamant-1-yl-4-(3-ethoxymethoxypropyl)phenyl]propen-(E)-yl}benzoic acid;
4-{2-[3-Adamant-1-yl-4-(3-ethoxymethoxypropyl)phenyl]propen-(Z)-yl}benzoic acid;
Ethyl 4-{2-[3-adamant-1-yl-4-(3-benzyloxypropyl)-phenyl]propen-(E/Z)-yl}-benzoate;
4-{2-[3-Adamant-1-yl-4-(3-benzyloxypropyl)phenyl]propen-(E)-yl}-benzoic acid;
4-{2-[3-Adamant-1-yl-4-(3-benzyloxypropyl)phenyl]-propen-(Z)-yl}benzoic acid;
Ethyl 4-{2-[3-adamant-1-yl-4-(3-diethylcarbamoyl-methoxypropyl)phenyl]propenyl}benzoate;
4-{2-[3-Adamant-1-yl-4-(3-diethylcarbamoylmethoxypropyl)phenyl]propenyl}benzoic acid;
Ethyl 4-{2-[3-adamant-1-yl-4-(3-carboxymethoxy-propyl)phenyl]propenyl}benzoate;
4-{2-[3-Adamant-1-yl-4-(3-carboxymethoxypropyl)-phenyl]propenyl}benzoic acid;
Ethyl 4-{2-[3-adamant-1-yl-4-(3-carbamoylmethoxypropyl)phenyl]propenyl}benzoate;
4-{2-[3-Adamant-1-yl-4-(3-carbamoylmethoxypropyl)phenyl]propenyl}benzoic acid;
N-Ethyl-4-[(E)-2-(3-(1-adamantyl)-4-methoxyethoxymethoxyphenyl)-1-propenyl]benzamide;
4-[(E)-2-(3-(1-Adamantyl)-4-methoxyethoxymethoxyphenyl)-1-propenyl]benzamide;
N-4-(Hydroxyphenyl)-4-[(E)-2-(3-(1-adamantyl)-4-methoxyethoxymethoxyphenyl)-1-propenyl]benzamide;
4-[(E)-2-(3-(1-Adamantyl)-4-methoxyethoxymethoxyphenyl)-1-propenyl]benzenemethanol;
4-[(E)-2-(3-(1-Adamantyl)-4-methoxyethoxymethoxyphenyl)-1-propenyl]benzaldehyde;
4-[(E)-2-(3-(1-Adamantyl)-4-methoxyethoxymethoxyphenyl)-1-propenyl]phenol;
4-[(E)-2-(3-(1-Adamantyl)-4-methoxyethoxymethoxyphenyl)-1-propenyl]benzoic acid morpholide; and
4-[(E)-2-(3-(1-Adamantyl)-4-methoxyethoxymethyl-sulphanylphenyl)-1-propenyl]benzoic acid.

* * * * *